US012765788B2

(12) United States Patent
Sano et al.

(10) Patent No.: US 12,765,788 B2
(45) Date of Patent: Oct. 20, 2026

(54) SPHYGMOMANOMETER

(71) Applicant: OMRON HEALTHCARE CO., LTD., Muko (JP)

(72) Inventors: Yoshihiko Sano, Kyoto (JP); Kosuke Abe, Kyoto (JP); Takanori Nishioka, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 383 days.

(21) Appl. No.: 18/585,117

(22) Filed: Feb. 23, 2024

(65) Prior Publication Data

US 2024/0237906 A1 Jul. 18, 2024

Related U.S. Application Data

(63) Continuation of application No. PCT/JP2023/008662, filed on Mar. 7, 2023.

(30) Foreign Application Priority Data

Mar. 16, 2022 (JP) ................................ 2022-041187

(51) Int. Cl.
*A61B 5/021* (2006.01)
*A61B 5/00* (2006.01)

(52) U.S. Cl.
CPC ...... *A61B 5/02141* (2013.01); *A61B 5/02116* (2013.01); *A61B 5/681* (2013.01);
(Continued)

(58) Field of Classification Search
CPC .... A61B 2560/0462; A61B 2562/0247; A61B 5/02; A61B 5/02116; A61B 5/02141;
(Continued)

(56) References Cited

U.S. PATENT DOCUMENTS

2011/0282222 A1 11/2011 Tseng et al.
2019/0298181 A1 10/2019 Iwata et al.
2019/0374115 A1 12/2019 Higashimura et al.

FOREIGN PATENT DOCUMENTS

CN 102170822 A 8/2011
CN 105852829 A 8/2016
(Continued)

OTHER PUBLICATIONS

Mar. 2, 2026 Examination Report issued in Indian Patent Application No. 202417006384.

(Continued)

*Primary Examiner* — Benjamin S Melhus
(74) *Attorney, Agent, or Firm* — Oliff PLC

(57) ABSTRACT

A sphygmomanometer includes a sensing cuff, and a back plate. The sensing cuff includes a first sheet extending in a circumferential direction of the site to be measured to cross an artery passing portion of the site to be measured, and a second sheet facing the first sheet. The sensing cuff has a bag shape formed by welding the first sheet and the second sheet. The back plate is disposed on the second sheet, extending along the circumferential direction of the site to be measured. A width direction dimension of the back plate measured in a width direction parallel to a direction in which the artery extends, is shorter than a width direction dimension of the sensing cuff, and is further shorter than an inner dimension between welding pools formed at end portions of an internal space of the sensing cuff.

6 Claims, 15 Drawing Sheets

(52) U.S. Cl.
CPC ...... *A61B 5/742* (2013.01); *A61B 2560/0462* (2013.01); *A61B 2562/0247* (2013.01)

(58) Field of Classification Search
CPC ..... A61B 5/022; A61B 5/02233; A61B 5/681; A61B 5/742; A61B 5/02225; A61B 5/0225; A61B 5/6824; A61B 5/0235; A61B 5/02125; A61B 5/6831; A61B 5/02108; A61B 2562/0219; A61B 5/0245; A61B 5/0507; A61B 5/02208; A61B 5/02255; A61B 5/6843; A61B 2505/07; A61B 2560/0223; A61B 2560/0406; A61B 2560/0443; A61B 5/0015; A61B 5/02007; A61B 5/02241; A61B 5/02438; A61B 5/02444; A61B 5/0261; A61B 5/0285; A61B 5/0295; A61B 5/05; A61B 5/053; A61B 5/117; A61B 5/1171; A61B 5/489; A61B 5/6823; A61B 5/7264; A61B 5/7275; A61B 10/00; A61B 2560/02; A61B 2562/0204; A61B 2562/168; A61B 2562/182; A61B 5/0022; A61B 5/023; A61B 5/0265; A61B 5/1072; A61B 5/11; A61B 5/1495; A61B 5/256; A61B 5/279; A61B 5/361; A61B 5/6802; A61B 5/6828; A61B 5/684; A61B 5/721; A61B 5/7235; A61B 5/7246; A61B 5/7289
See application file for complete search history.

(56) References Cited

FOREIGN PATENT DOCUMENTS

| | | | |
|---|---|---|---|
| CN | 110113992 | A | 8/2019 |
| CN | 110897276 | A | 3/2020 |
| CN | 112171009 | A | 1/2021 |
| JP | 2018-102872 | A | 7/2018 |
| JP | 2019-025531 | A | 2/2019 |

OTHER PUBLICATIONS

Sep. 10, 2024 International Preliminary Report on Patentability issued in International Patent Application No. PCT/JP2023/008662.
May 16, 2023 International Search Report issued in International Patent Application No. PCT/JP2023A/008662.
Jul. 31, 2026 Office Action issued in Chinese Patent Application No. 202380013329.9.

SPHYGMOMANOMETER

CROSS-REFERENCE TO RELATED APPLICATIONS

This application claims benefit of priority to Japanese Patent Application 2022-41189, filed Mar. 16, 2022, the entire content of which is incorporated herein by reference.

TECHNICAL FIELD

The present invention relates to a sphygmomanometer, and more particularly to a sphygmomanometer that is worn while surrounding a site to be measured in a circumferential direction.

BACKGROUND ART

Conventionally, as this type of sphygmomanometer, for example, there is a sphygmomanometer disclosed in Patent Document 1 (JP-A-2018-102872). The sphygmomanometer includes a pump, a sensing cuff in contact with the human body, a pressing cuff that presses the sensing cuff, and a plate-shaped back plate provided between the sensing cuff and the pressing cuff. In this sphygmomanometer, the sensing cuff is pressed flat against the human body, and wrinkles, folds, blocking of air, and the like generated in the sensing cuff in a wrist shape, the softness of the human body, or a pressed state are prevented to improve blood pressure measurement accuracy. The plate-shaped back plate has a width larger than the sensing cuff width to enhance the stability of the sensing cuff, and is curved and thinned from the center of the sensing cuff toward the end of the sensing cuff to follow the pressed shape of the human body in the pressed state, thereby further enhancing the blood pressure measurement accuracy.

In the sphygmomanometer as described above, the sensing cuff includes an airbag obtained by sticking together the thin film sheets such as mainly polyurethane (PU), polyvinyl chloride (PVC), and ethylene vinyl acetate (EVA) by high-frequency welding or heat welding. The welding portion in the sensing cuff is hard because the sheets are melted and coupled to each other, and the remaining melted portion has a hard portion because the remaining melted portion protrudes into the bag as a welding pool.

SUMMARY OF THE INVENTION

In such a conventional technique, when the sensing cuff is pressed against the human body with the back plate, the welding portion and the welding pool of the thin film sheet constituting the sensing cuff locally apply high pressure to the human body, and a high-pressure distribution is generated in a portion different from the portion where the blood pressure information is measured. As a result, accurate blood pressure information purely generated from the human body pulse wave is hardly transmitted to the sensing cuff, and an accurate human body pressure pulse wave in the entire portion in contact with the sensing cuff cannot be measured.

Therefore, an object of the present invention is to provide a sphygmomanometer capable of accurately measuring a human body pressure pulse wave by a sensing cuff so that a portion where a welding pool at an end portion of the sensing cuff is present does not press the human body.

In order to solve the above problem, a sphygmomanometer according to the present disclosure includes:

a sensing cuff including, when being worn on a site to be measured, a first sheet extending in a circumferential direction of the site to be measured to cross an artery passing portion of the site to be measured, and a second sheet facing the first sheet, the sensing cuff having a bag shape formed by welding the first sheet and the second sheet; and a back plate disposed on the second sheet, extending along the circumferential direction of the site to be measured, and conveying a pressing force to the sensing cuff, wherein a width direction dimension of the back plate measured in a width direction perpendicular to the circumferential direction of the site to be measured, is shorter than a width direction dimension of the sensing cuff, and is further shorter than an inner dimension between welding pools formed at end portions of an internal space of the sensing cuff.

With respect to the sphygmomanometer of the present disclosure, a width direction dimension of the back plate measured in a width direction perpendicular to the circumferential direction of the site to be measured, is shorter than a width direction dimension of the sensing cuff. Furthermore, the width direction dimension of the back plate is further shorter than an inner dimension between welding pools formed at end portions of an internal space of the sensing cuff. Therefore, when the sensing cuff is pressed by the back plate, hard portions where the welding pools are present are not pressed by the back plate, and a strong stress is hardly generated. As a result, a high pressure distribution is not generated in a portion different from a portion where blood pressure information is measured at the site to be measured, and it is possible to measure an accurate human body pressure pulse wave by the sensing cuff.

DETAILED DESCRIPTION

Hereinafter, embodiments of the present invention will be described in detail with reference to the drawings.

(Configuration of Sphygmomanometer)

Figure 1:
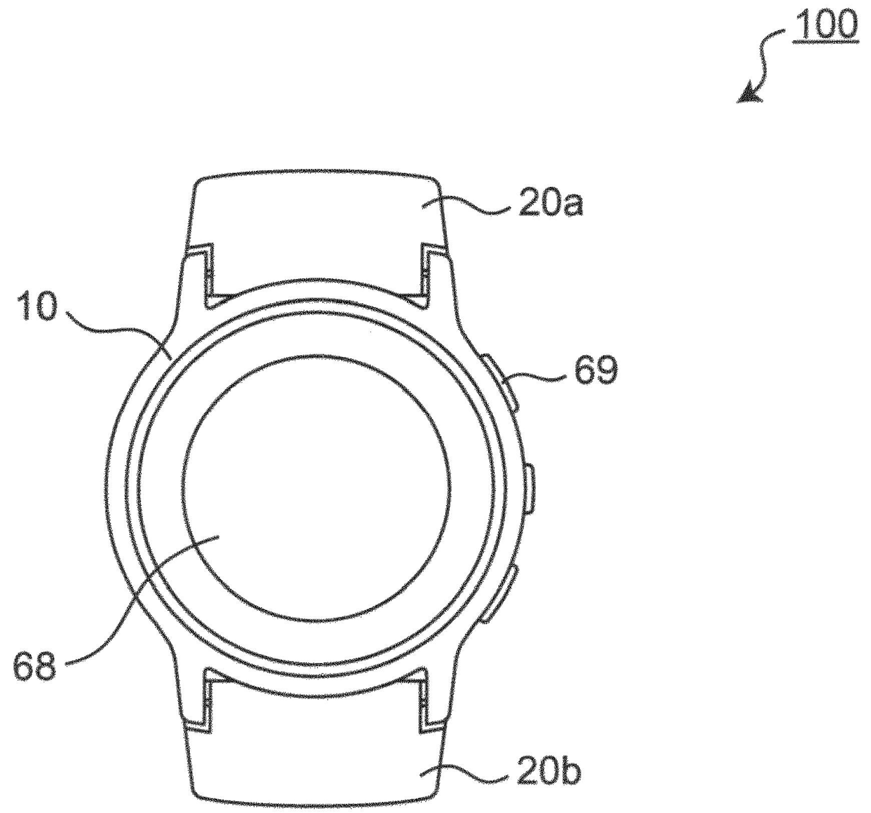
FIG. 1 is a front view showing a schematic external configuration of a sphygmomanometer according to an embodiment.
Figure 2:
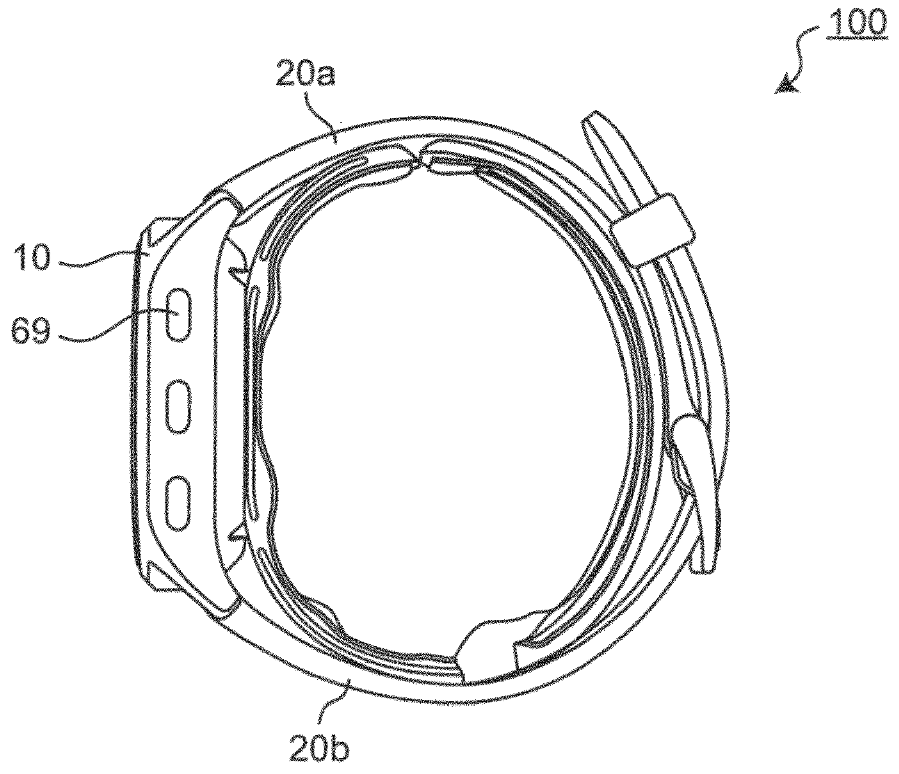
FIG. 2 is a side view showing a schematic external configuration of the sphygmomanometer according to the embodiment.
Figure 3:
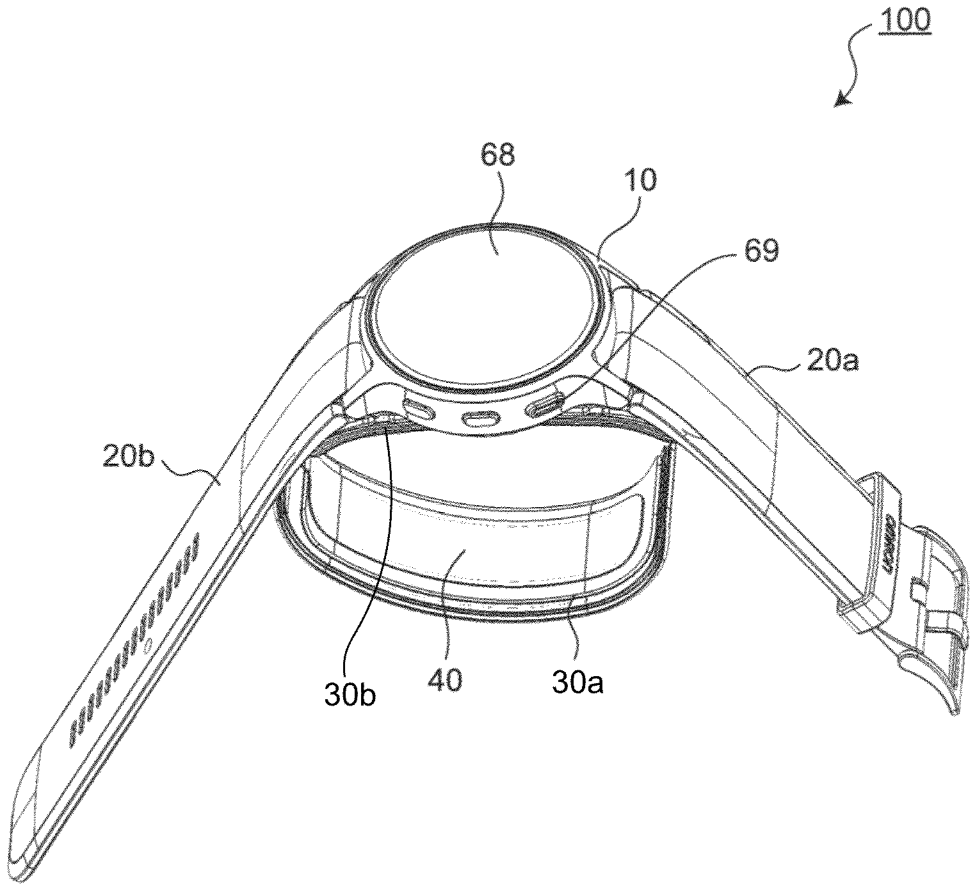
FIG. 3 is a perspective view showing a schematic external configuration of the sphygmomanometer according to the embodiment.

FIG. 1 shows a configuration of a sphygmomanometer 100 according to the present embodiment as viewed from the front. FIG. 2 shows a configuration of the sphygmomanometer 100 as viewed from the side. In addition, FIG. 3 shows a configuration of the sphygmomanometer 100 as viewed from an oblique direction in a state where a belt described below is opened. A schematic external configuration of the sphygmomanometer 100 will be described with reference to FIGS. 1 to 3.

Figure 4:
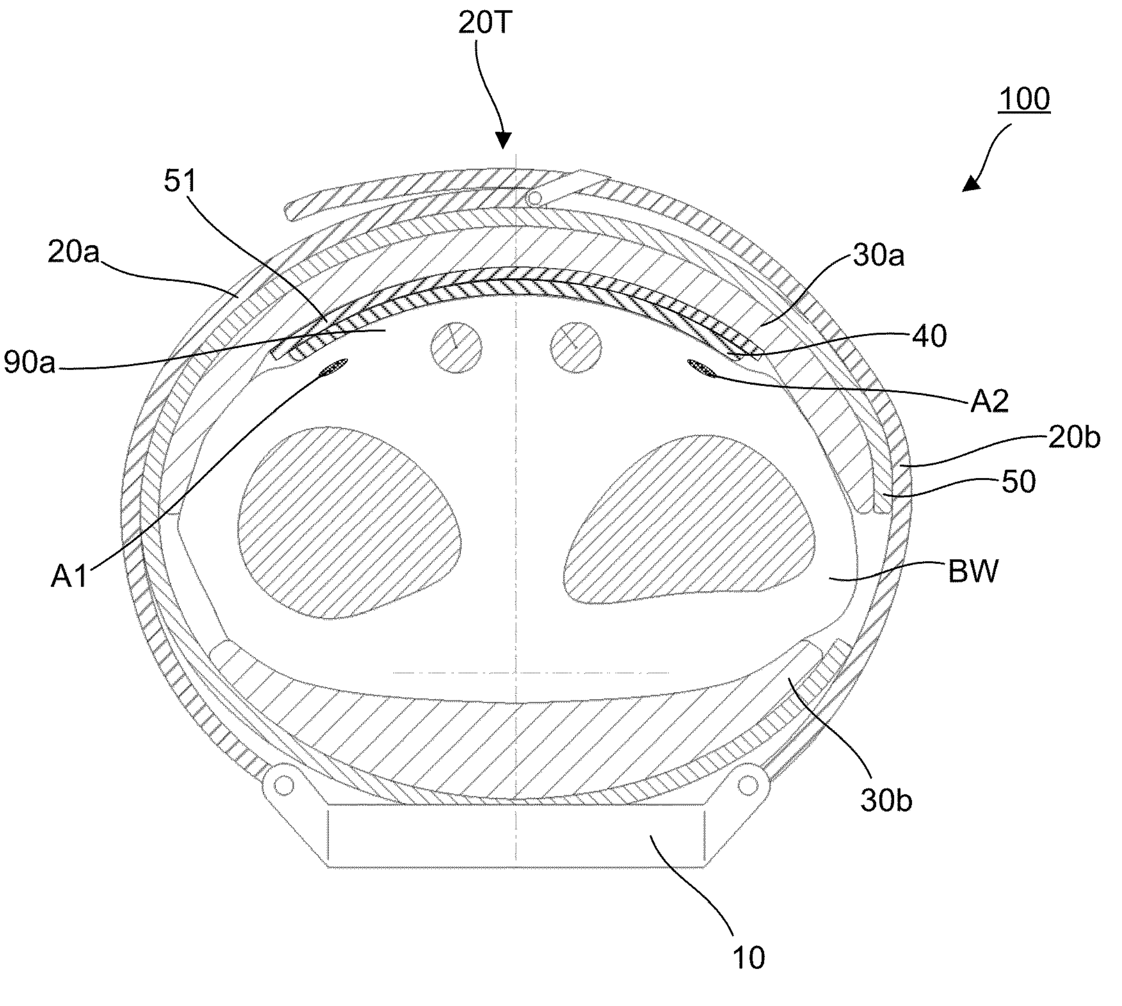
FIG. 4 is a cross-sectional view showing a state in which the sphygmomanometer according to the embodiment is worn on the wrist.

The sphygmomanometer 100 includes a main body 10 and two belts 20*a* and 20*b* extending from the main body 10, and surrounding and worn on the site to be measured (in this example, as shown in FIG. 4 to be described below, a left wrist BW is scheduled as a site to be measured). By fastening the one belt 20*a* and the other belt 20*b*, a state in which the sphygmomanometer 100 is worn on the site to be measured (see FIG. 4, which is referred to as "worn state") is created. In addition, as shown in FIGS. 1 to 3, the main body 10 includes a display device 68 and an operation device 69 including a plurality of buttons. Furthermore, the main body 10 is mounted with a pump to be described below.

In addition, as shown in FIG. 3, the sphygmomanometer 100 includes pressing cuffs 30*a* and 30*b* and a sensing cuff 40. It should be noted that the pressing cuff 30*a* is a pressing cuff positioned on the site to be measured side close to the artery, and the pressing cuff 30*b* is a pressing cuff positioned on the main body 10 side opposite to the site to be measured side.

In the present embodiment, the pressing cuffs 30*a* and 30*b* and the sensing cuff 40 constitute a cuff structure having a laminated structure. In the worn state of the sphygmomanometer 100, the pressing cuff 30*a* and the sensing cuff 40 are arranged in this order as viewed from the fastening portion 20T side of the belts 20*a* and 20*b*. In addition, the pressing cuff 30*b* is disposed on the main body 10 side.

As shown in FIG. 4, the cuff structure according to the present embodiment further includes a curler 50 and a back plate 51. The curler 50 is, for example, a member made of a resin plate having a certain degree of flexibility and hardness and having a shape curved along the circumferential direction surrounding the site to be measured in a natural state. The pressing cuff 30*a* is disposed on the inner peripheral side of the curler 50 and on the side corresponding to the site to be measured, and the pressing cuff 30*b* is disposed on the inner peripheral side of the curler 50 and on the side closer to the main body 10 on the side opposite to the site to be measured. In addition, the cuff structure includes a back plate 51 between the pressing cuff 30*a* and the sensing cuff 40. A member including the belts 20*a* and 20*b*, the curler 50, the pressing cuffs 30*a* and 30*b*, and the back plate 51 functions as a pressing member that generates a pressing force on the site to be measured. The pressing member including the pressing cuffs 30*a* and 30*b* presses the sensing cuff 40 toward the site to be measured and causes the sensing cuff 40 to press the site to be measured.

FIG. 4 cross-sectionally shows a state in which the sphygmomanometer 100 is worn on the wrist BW, which is a site to be measured. As shown in FIG. 4, the pressing cuff 30*a* constituting the pressing member has a bag shape and is disposed between the belts 20*a* and 20*b* and the sensing cuff 40. In addition, the pressing cuff 30*b* also has a bag shape, and is disposed at a position opposite to the pressing cuff 30*a* so as to sandwich the wrist BW between the pressing cuff 30*a* and the pressing cuff 30*b*.

As described above, the belts 20*a* and 20*b* surround the wrist BW in the circumferential direction, whereby the sphygmomanometer 100 is worn on the wrist BW. In the worn state of the present embodiment, as shown in FIG. 4, the curler 50, the pressing cuff 30*b*, the wrist BW, the sensing cuff 40, the back plate 51, and the pressing cuff 30*a* are arranged in this order from the main body 10 toward the fastening portion 20T of the belts 20*a* and 20*b*. In the configuration example in FIG. 4, the main body 10 is disposed at a portion opposite to the sensing cuff 40 in the circumferential direction of the belts 20*a* and 20*b*.

In the worn state, the bag-shaped pressing cuffs 30*a* and 30*b* extend, for example, along the circumferential direction of the wrist BW. In addition, the bag-shaped sensing cuff 40 is disposed on the inner circumferential side of the belts 20*a* and 20*b* with respect to the pressing cuff 30*a*, is in contact with (indirectly or directly) the wrist BW, and extends in the circumferential direction so as to cross the artery passing portion 90*a* of the wrist BW. It should be noted that the "inner circumferential side" of the belts 20*a* and 20*b* refers to a side facing the wrist BW in a worn state surrounding the wrist BW.

FIG. 4 shows a radial artery A1 and an ulnar artery A2 of the wrist BW. The pressing cuffs 30*a* and 30*b* constituting the pressing member press the sensing cuff 40 toward the wrist BW to cause the sensing cuff 40 to press the wrist BW.

Figure 5:
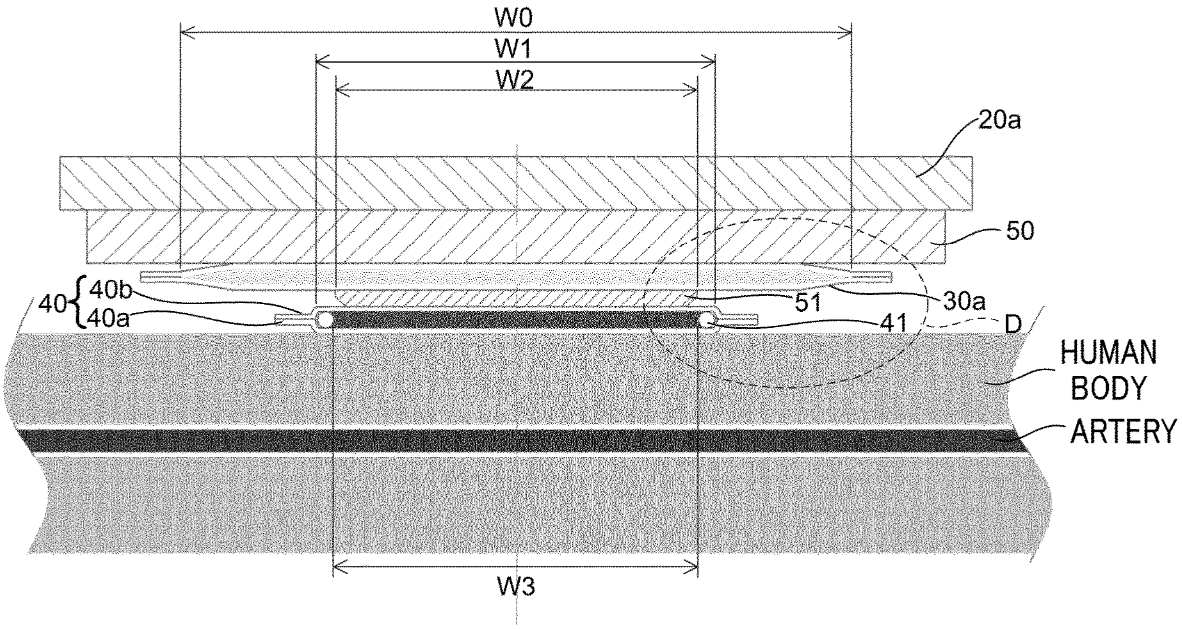
FIG. 5 is a cross-sectional view of a belt, a curler, a pressing cuff, a back plate, and a sensing cuff along the direction in which the artery of the subject extends.

FIG. 5 is a cross-sectional view of the belt 20*a*, the curler 50, the pressing cuff 30*a*, the back plate 51, and the sensing cuff 40 along the direction in which the artery of the subject extends.

Figure 8:
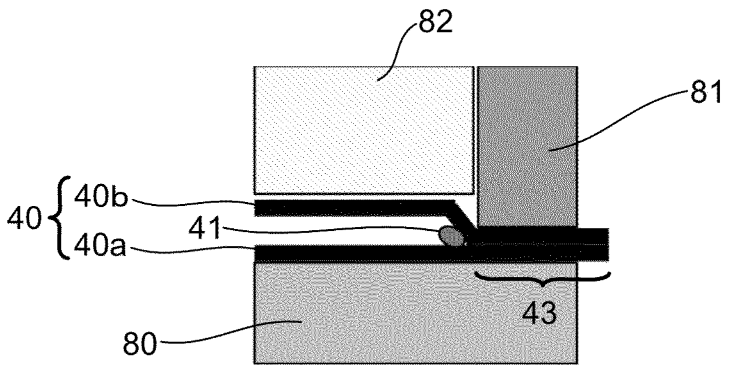
FIG. 8 is a view for illustrating the manufacturing process of the sensing cuff.

As shown in FIGS. 5 and 8, the sensing cuff 40 includes a first sheet 40*a* on a side in contact with the wrist BW and a second sheet 40*b* facing the first sheet 40*a*. The first sheet 40*a* and the second sheet 40*b* are thin film sheets mainly made of polyurethane (PU), polyvinyl chloride (PVC), ethylene vinyl acetate (EVA), thermoplastic polyurethane (TPU), or the like; and the sensing cuff 40 is formed in a bag shape by sticking the peripheral edge portions 43 of the first sheet 40*a* and the second sheet 40*b* together, and bringing them in close contact by high-frequency welding or heat welding.

As shown in FIG. 5, the width direction dimension W1 of the sensing cuff 40 is a dimension of a portion excluding the peripheral edge portion 43.

Figure 6:
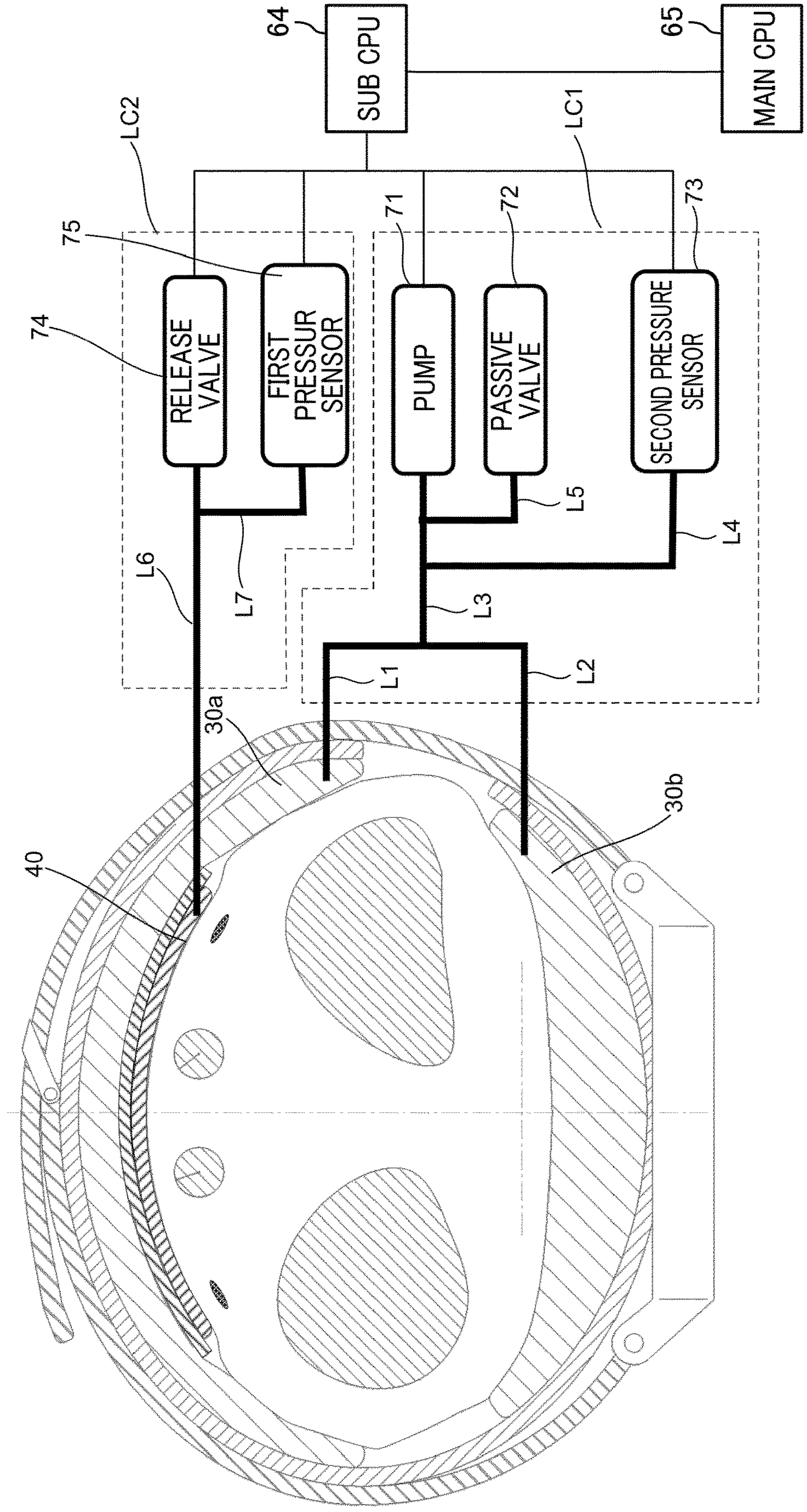
FIG. 6 is a diagram showing a schematic configuration related to a flow path system of the sphygmomanometer according to the embodiment.

As shown in FIG. 6, a release valve 74 and a first pressure sensor 75 for detecting the pressure of the sensing cuff 40 are attached to the sensing cuff 40.

In the present embodiment, a solenoid-type release valve is used as the release valve 74 as an example. The release valve 74 is inserted into the sensing cuff 40 and is set to any one of an open state and a closed state under the control of a sub CPU 64 described below. When the release valve 74 is in the open state, the valve port of the release valve 74 is opened, the inside of the sensing cuff 40 comes into a state of conducting to the outside air, and the pressure inside the sensing cuff 40 is released to the atmospheric pressure. In addition, when the release valve 74 is in the closed state, the valve port of the release valve 74 is closed, and the inside of the sensing cuff 40 is in a non-conductive state with the outside air.

In this example, the first pressure sensor 75 includes a piezoresistive pressure sensor. The first pressure sensor 75 is inserted into the sensing cuff 40 and detects a pressure value in the sensing cuff 40. The pressure value detected by the first pressure sensor 75 is read by the sub CPU 64.

As described above, the control of the open state and the closed state of the release valve 74 and the detection of the pressure of the sensing cuff 40 using the first pressure sensor 75 are performed by the sub CPU 64. It should be noted that the main CPU 65 described below mainly controls the operation of the entire sphygmomanometer 100.

As shown in FIG. 5, a back plate 51 is inserted between the pressing cuff 30*a* and the sensing cuff 40. The back plate 51 is formed of, for example, a plate-shaped material having a thickness of about 0.7 mm, extends along the circumferential direction of the site to be measured, and has a function of transmitting the pressing force from the pressing cuffs 30*a* and 30*b* to the sensing cuff 40. It should be noted that as a material of the back plate 51, a resin such as polypropylene, polyethylene terephthalate (PET), or PVC, or an elastomer such as thermoplastic elastomer (TPE) or TPU may be used.

In a cross-sectional view along the direction in which the artery extends, the width direction dimension W2 of the back plate 51 is shorter than the width direction dimension W1 of the sensing cuff 40. Welding pools 41 are formed in the internal space formed in the bag shape of the sensing cuff 40, and a width direction dimension from an end surface of one welding pool 41 to an end surface of the other welding pool 41 is defined as an effective width direction dimension W3 of the sensing cuff 40. Details of the welding pool 41 of the sensing cuff 40, the relationship between the width direction dimension W1 of the sensing cuff 40 and the width direction dimension W2 of the back plate 51, the positional relationship between the welding portion where the welding pool 41 is formed and the end surface of the back plate 51, and the effective width direction dimension W3 of the sensing cuff 40 will be described below.

FIG. 6 is a diagram showing a schematic configuration related to a flow path system of the sphygmomanometer 100. As shown in FIG. 6, the flow path system of the sphygmomanometer 100 includes a fluid circuit LC1 connected to the pressing cuffs 30*a* and 30*b* and a fluid circuit LC2 connected to the sensing cuff 40.

The fluid circuit LC1 includes a pump 71, a passive valve 72, a second pressure sensor 73, and respective flow paths L1 to L5. Air circulates in each of the flow paths L1 to L5. In the fluid circuit LC1, according to on/off (supply/stop of air) of the pump 71 under the control of the sub CPU 64, air is supplied to the pressing cuffs 30*a* and 30*b* to expand them or air is discharged from the pressing cuffs 30*a* and 30*b*. When the pressing cuffs 30*a* and 30*b* are expanded, the pump 71 is set to the ON state under the control of the sub CPU 64, air is supplied from the pump 71 to the pressing cuffs 30*a* and 30*b* through the flow paths L3, L1, and L2, and the pressure in the pressing cuffs 30*a* and 30*b* is detected by the second pressure sensor 73 and the sub CPU 64 through the flow path L4. It should be noted that at this time, since the passive valve 72 is pressurized through the flow path L5, the passive valve 72 functions as a check valve, and the air in the pressing cuffs 30*a* and 30*b* is not discharged to the outside through the flow path L5. On the other hand, when the air is discharged from the pressing cuffs 30*a* and 30*b*, the pump 71 is set to the OFF state under the control of the sub CPU 64, and the passive valve 72 is not pressurized through the flow path L5. Therefore, the air in the pressing cuffs 30*a* and 30*b* is discharged from the passive valve 72 through the flow paths L1, L2, L3, and L5, and the pressure in the pressing cuffs 30*a* and 30*b* is released to the atmospheric pressure.

The fluid circuit LC2 includes a release valve 74, a first pressure sensor 75, and respective flow paths L6 to L7. Air circulates in each of the flow paths L6 to L7. In the fluid circuit LC2, according to the off/on (opening/closing of the valve) of the release valve 74 under the control of the sub CPU 64, the air in the sensing cuff 40 is discharged or the discharge of the air from within the sensing cuff 40 is prevented. When the air in the sensing cuff 40 is discharged, the release valve 74 is set to the OFF state (open state) under the control of the sub CPU 64, the air in the sensing cuff 40 is discharged through the flow paths L6 and L7 and the release valve 74, and the pressure in the sensing cuff 40 is released to the atmospheric pressure. On the other hand, when the discharge of the air from the sensing cuff 40 is prevented, the release valve 74 is set to the ON state (closed state) under the control of the sub CPU 64, and the discharge of the air from the sensing cuff 40 through the flow paths L6 and L7 and the release valve 74 is prevented. When the release valve 74 is set to the ON state (closed state), a change in pressure in the sensing cuff 40 is detected by the first pressure sensor and the sub CPU 64 through the flow paths L6 and L7, and blood pressure measurement becomes possible.

Figure 7:
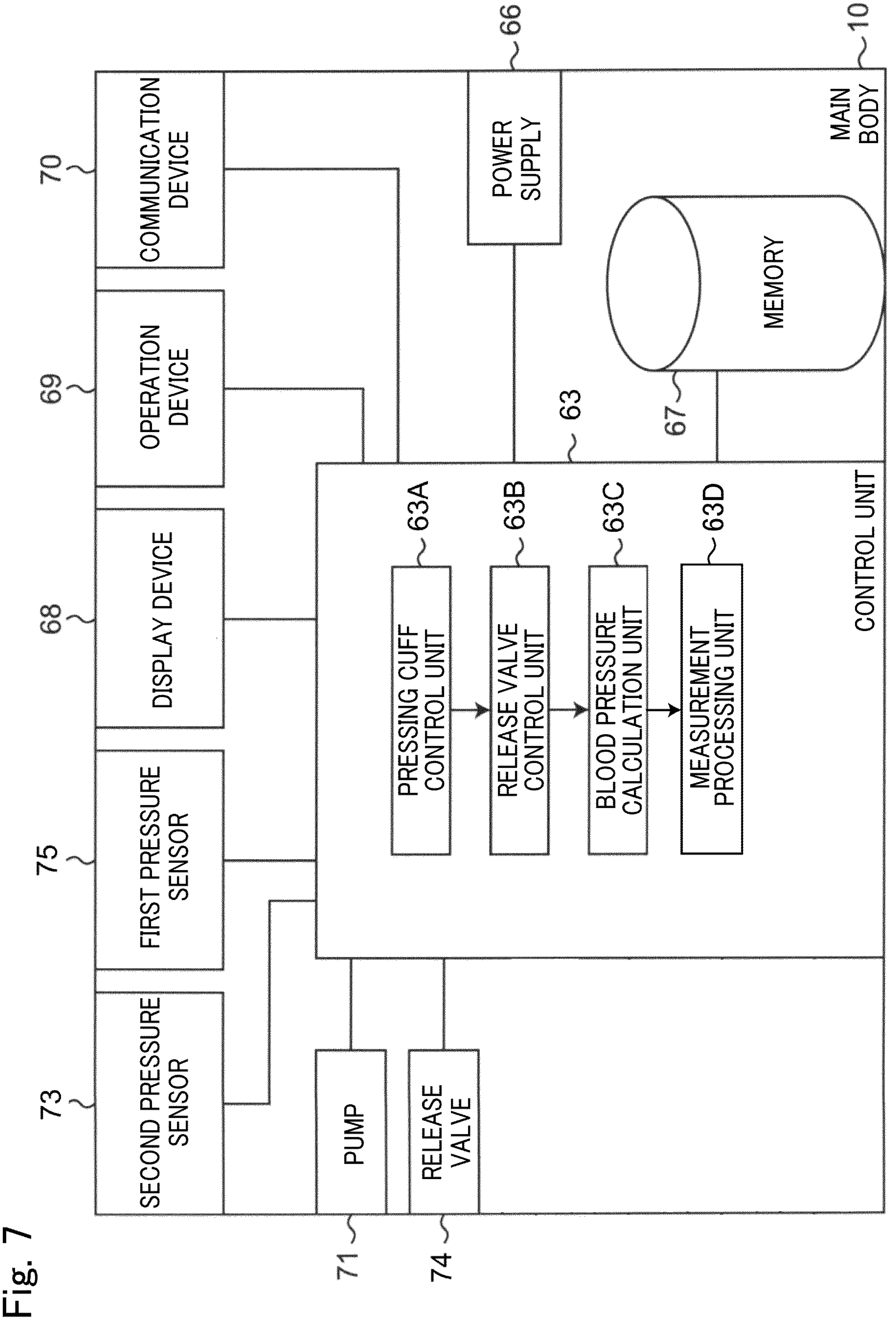
FIG. 7 is a diagram showing a schematic configuration related to a control system of the sphygmomanometer according to the embodiment.

FIG. 7 shows a schematic configuration related to a control system of the sphygmomanometer 100. As shown in FIG. 7, the main body 10 of the sphygmomanometer 100 includes a control unit 63 that performs control, and a plurality of components to be controlled 66 to 75 controlled by the control unit 63.

In FIG. 7, the sub CPU 64 and the main CPU 65 are collectively referred to as a control unit 63. In addition, the plurality of components to be controlled include a power supply 66, a memory 67, a display device 68, an operation device 69, a communication device 70, a pump 71, a second pressure sensor (pressing cuff pressure sensor) 73, a release valve 74, and a first pressure sensor (sensing cuff pressure sensor) 75.

In this example, the power supply 66 is made of a rechargeable secondary battery. The power supply 66 supplies power for driving to elements mounted on the main body 10, for example, the control unit 63, the memory 67, the display device 68, the communication device 70, the pump 71, the second pressure sensor 73, the release valve 74, and the first pressure sensor 75.

The memory 67 stores various types of data. For example, the memory 67 can store measured values measured by the sphygmomanometer 100, measurement results of the second pressure sensor 73 and the first pressure sensor 75, and the like. In addition, the memory 67 can also store various types of data generated by the control unit 63. The memory 67 includes a random access memory (RAM), a read only memory (ROM), and the like. For example, various programs are changeably stored in the memory 67.

The display device 68 includes, for example, a liquid crystal display (LCD). The display device 68 displays information related to blood pressure measurement such as a blood pressure measurement result or other information according to a control signal from the control unit 63. It should be noted that the display device 68 may have a function as a touch panel.

The operation device 69 includes a plurality of buttons that receive instructions from the user. When the operation device 69 receives an instruction from the user, an operation/movement according to the instruction is performed under the control of the control unit 63. It should be noted that the operation device 69 may be, for example, a pressure-sensitive (resistive) or proximity (capacitive) touch panel switch. In addition, a configuration in which a microphone (not shown) is provided to receive an instruction by a user's voice may be adopted.

The communication device 70 transmits various types of data and various signals to an external device through a communication network, and receives information from the external device through the communication network. The network may be wireless communication or wired communication.

In this example, the pump 71 includes a piezoelectric pump, and is driven based on a control signal given from the control unit 63. The pump 71 can supply the pressurizing fluid to the pressing cuffs 30*a* and 30*b* through respective flow paths described below. Here, any liquid or any gas can be adopted as the fluid. In the present embodiment, the fluid is air (hereinafter, the fluid is described as air).

The second pressure sensor 73 and the first pressure sensor 75 include, for example, piezoresistive pressure sensors. The second pressure sensor 73 detects the pressure in the pressing cuffs 30*a* and 30*b* through the flow path L4 shown in FIG. 6. The first pressure sensor 75 detects the pressure in the sensing cuff 40 through the flow path L7 shown in FIG. 6.

The release valve 74 is controlled according to the movement of the pump 71. That is, the opening and closing of the passive valve 72 are controlled according to the on/off (supply/stop of air) of the pump 71. For example, the passive valve 72 closes when the pump 71 is turned on. On the other hand, the passive valve 72 opens when the pump 71 is turned off.

The release valve 74 is connected to the flow path L6 shown in FIG. 6, and is controlled to any one of an open state and a closed state based on a control signal given from the sub CPU 64 as the control unit 63. When the release valve 74 is set to the OFF state and in the open state, the air in the sensing cuff 40 is discharged from the release valve 74 through the flow path L6, and the pressure in the sensing cuff 40 is released to the atmospheric pressure. On the other hand, when the release valve 74 is set to the ON state and in the closed state, the discharge of air from the release valve 74 is prevented.

In this example, the control unit 63 includes a sub central processing unit (CPU) 64 and a main CPU 65. For example, the control unit 63 reads each program and each piece of data stored in the memory 67. In addition, the control unit 63 controls each of the units 67 to 75 according to the read program to cause each of the units 67 to 75 to execute a predetermined movement (function). In addition, the control unit 63 performs predetermined calculation, analysis, processing, and the like in the control unit 63 according to the read program. It should be noted that a part or the whole of each function executed by the control unit 63 may be configured in hardware with one or more integrated circuits or the like.

As shown in FIG. 7, the control unit 63 according to the present embodiment includes a pressing cuff control unit 63A, a release valve control unit 63B, a blood pressure calculation unit 63C, and a measurement processing unit 63D as functional blocks. The pressing cuff control unit 63A controls the pressing cuffs 30*a* and 30*b* to any one of a pressed state in which air is supplied to the pressing cuffs 30*a* and 30*b* to press the site to be measured through the pressing cuffs 30*a* and 30*b* and a released state in which air is discharged from the pressing cuffs 30*a* and 30*b* to release the pressing of the site to be measured through the pressing cuffs 30*a* and 30*b*. The release valve control unit 63B controls the release valve 74 to any one of an open state and a closed state. The blood pressure calculation unit 63C calculates the blood pressure based on the pressure of the air accommodated in the sensing cuff 40 when the release valve 74 is in the closed state.

(Welding Portion of Sensing Cuff)

Next, the welding portion of the sensing cuff 40 in the present embodiment will be described with reference to FIGS. 8 to 10. FIG. 8 is a view for illustrating the manufacturing process of the sensing cuff 40, and FIGS. 9 and 10 are micrographs obtained by photographing a welding portion.

As shown in FIG. 8, in the manufacturing process of the sensing cuff 40, first, the peripheral edge portions 43 of the first sheet 40*a* and the second sheet 40*b*, which are thin sheets such as thermoplastic polyurethane (TPU) and polyvinyl chloride (PVC), are stuck together. Then, the peripheral edge portion 43 is sandwiched between the lower type welding electrode 80 and the upper type welding electrode 81, and further, the second sheet 40*b* is prevented from escaping upward by the presser jig 82. Then, by energizing the lower type welding electrode 80 and the upper type welding electrode 81, the peripheral edge portions 43 of the first sheet 40*a* and the second sheet 40*b* are brought into close contact with each other by high-frequency welding or heat welding, and the sensing cuff 40 is formed into a bag shape.

In this case, when the first sheet 40*a* and the second sheet 40*b* are sandwiched and welded between the upper type welding electrode 81 and the lower type welding electrode 80, the material surfaces of these sheets are melted, and the remaining welding portion protrudes. As a result, as shown in FIG. 9, a welding pool 41 is formed on the inside near the peripheral edge portion 43 of the sensing cuff 40. The size and shape of the welding pool 41 can be changed depending on the welding method. For example, the size of the welding pool 41 can be changed by the time of pressing by the presser jig 82, the current value supplied to the lower type welding electrode 80 and the upper type welding electrode 81, and the like. However, the welding pool 41 has a feature of occurring in any case regardless of the size and being very hard.

Figure 9:
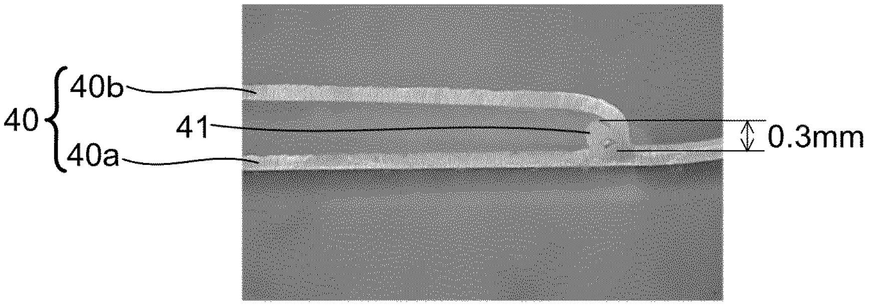
FIG. 9 is a micrograph obtained by photographing a welding portion in the sensing cuff.
Figure 10:
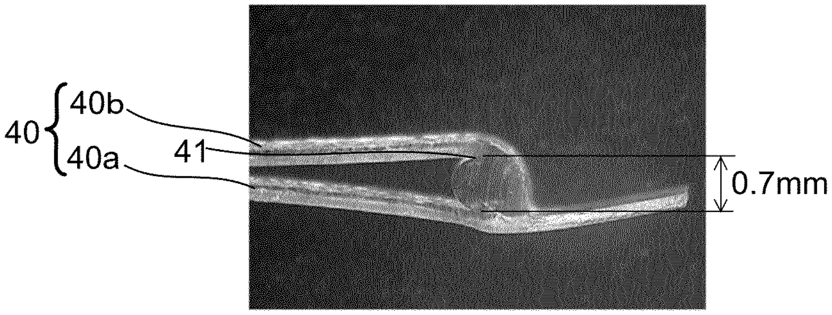
FIG. 10 is a micrograph obtained by photographing a welding portion in the sensing cuff.

FIG. 9 is a micrograph when the height of the welding pool 41 in the direction from the first sheet 40*a* toward the second sheet 40*b* is 0.3 mm. In addition, FIG. 10 is a micrograph when the height of the welding pool 41 in the direction from the first sheet 40*a* toward the second sheet 40*b* is 0.7 mm.

(Configurations of Back Plate and Sensing Cuff)

Figure 11:
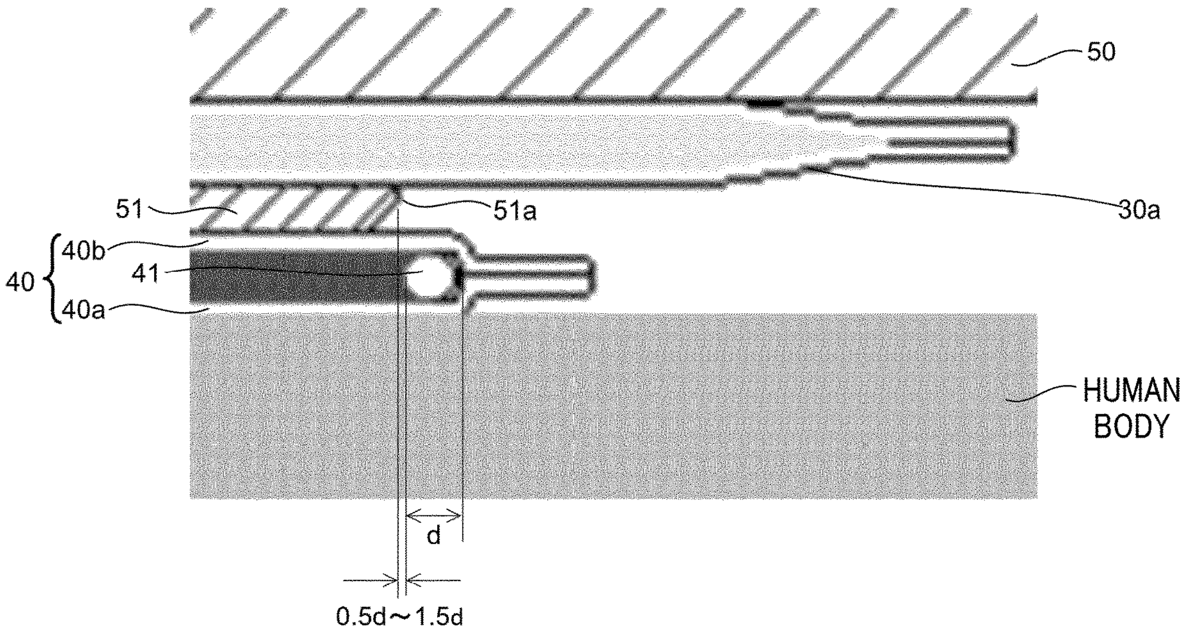
FIG. 11 is an enlarged view of a portion D near the welding pool in FIG. 5, and is a view before blood pressure measurement.
Figure 12:
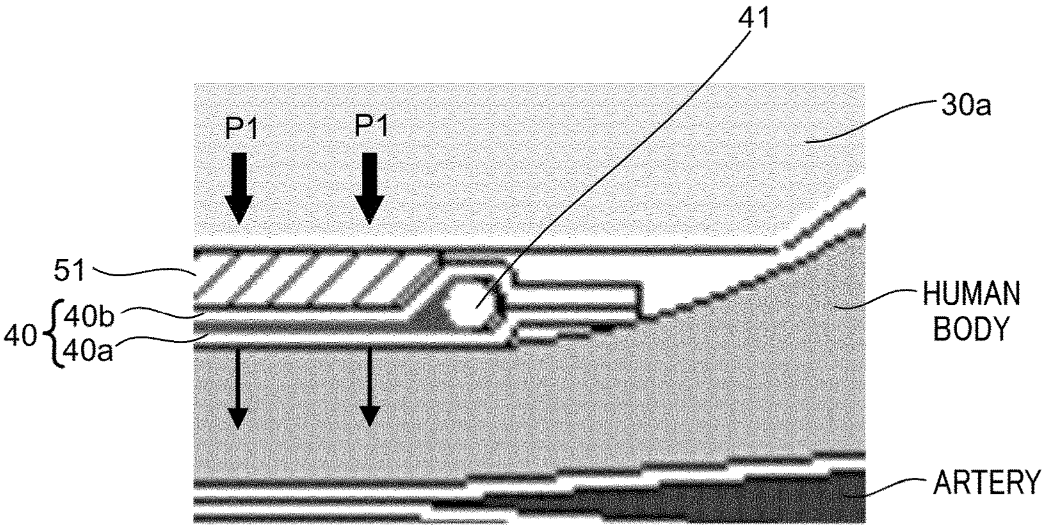
FIG. 12 is an enlarged view of a portion D near the welding pool in FIG. 5, and is a view at the time of blood pressure measurement.

Next, a positional relationship between the back plate 51 and the sensing cuff 40 will be described with reference to FIGS. 5, 11, and 12. FIG. 11 is an enlarged view of a portion D near the welding pool 41 in FIG. 5, and is a view before blood pressure measurement. FIG. 12 is an enlarged view of a portion D near the welding pool 41 in FIG. 5, and is a view at the time of blood pressure measurement.

First, as shown in FIG. 5, in the cross-sectional view along the direction in which the artery extends, the width direction dimension W2 of the back plate 51 is set to be shorter than the width direction dimension W1 of the sensing cuff 40 to avoid the welding pool 41 of the sensing cuff 40.

Next, as shown in FIG. 11, the shape of the end surface 51*a* of the back plate 51 is formed in a C surface shape or an R surface shape to avoid the welding pool 41.

Furthermore, as shown in FIG. 11, when the first sheet 40*a* and the second sheet 40*b* are joined by welding, and the end surface on the internal space side of the sensing cuff 40 at the joined portion is referred to as a joining end surface, and when the width direction dimension from the joining end surface to the end surface of the welding pool 41 is denoted by d, a distance between the end surface 51*a* of the back plate 51 and the end surface of the welding pool 41 is set to be 0.5d to 1.5d. Details of the reason why the distance between the end surface 51*a* of the back plate 51 and the end surface of the welding pool 41 is set in this manner will be described below.

In the present embodiment, as a result of configuring the back plate 51 and the sensing cuff 40 in this manner, the following functions are exhibited. As shown in FIG. 12, when a pressing force is applied to the sensing cuff 40 as indicated by an arrow P1 by the pressing cuffs 30*a* and 30*b* and the back plate 51 at the time of measurement, the back plate 51 presses the sensing cuff 40 while avoiding the hard welding pool 41, and thus a strong stress is less likely to occur near the welding portion where the welding pool 41 is formed. Therefore, a uniform distribution can be obtained as the pressure distribution with respect to the sensing cuff 40.

(Comparative Example)

In order to further clarify the advantages obtained by the configurations of the back plate 51 and the sensing cuff 40 of the present embodiment, as a comparative example, the configurations of the back plate 51' and the sensing cuff 40 in the conventional sphygmomanometer will be described with reference to FIGS. 13 and 14.

Figure 13:
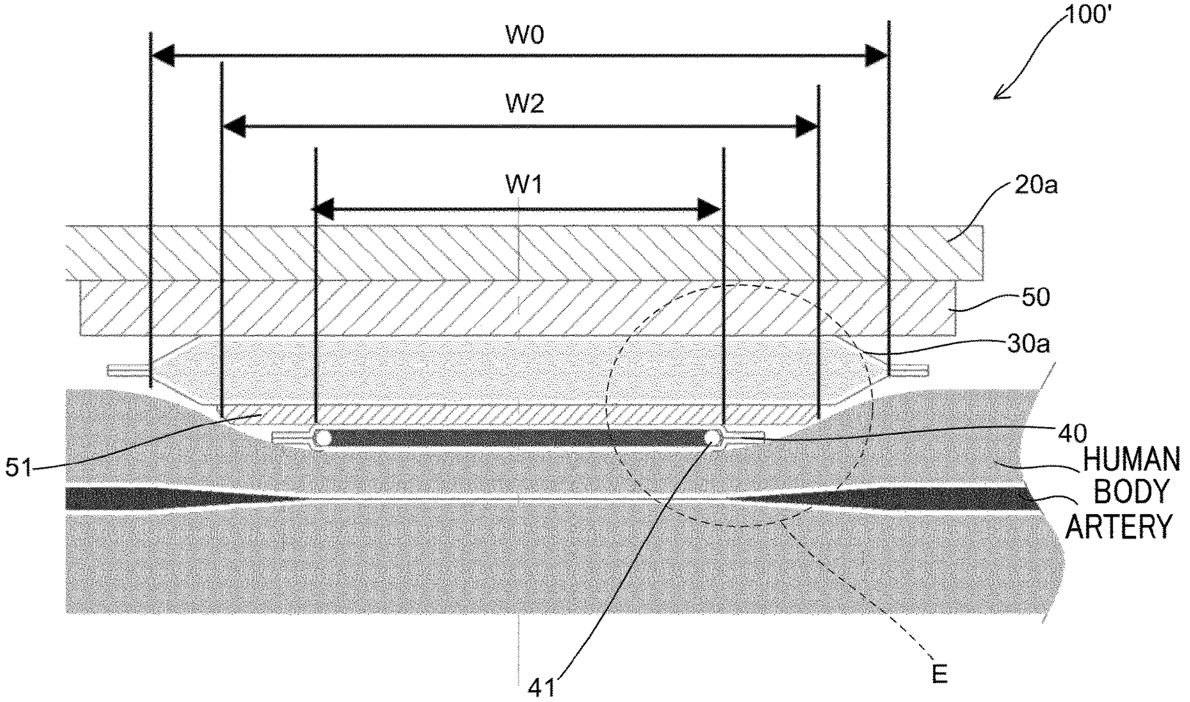
FIG. 13 is a cross-sectional view of a belt, a curler, a pressing cuff, a back plate, and a sensing cuff along the direction in which the artery of the subject extends in a comparative example.
Figure 14:
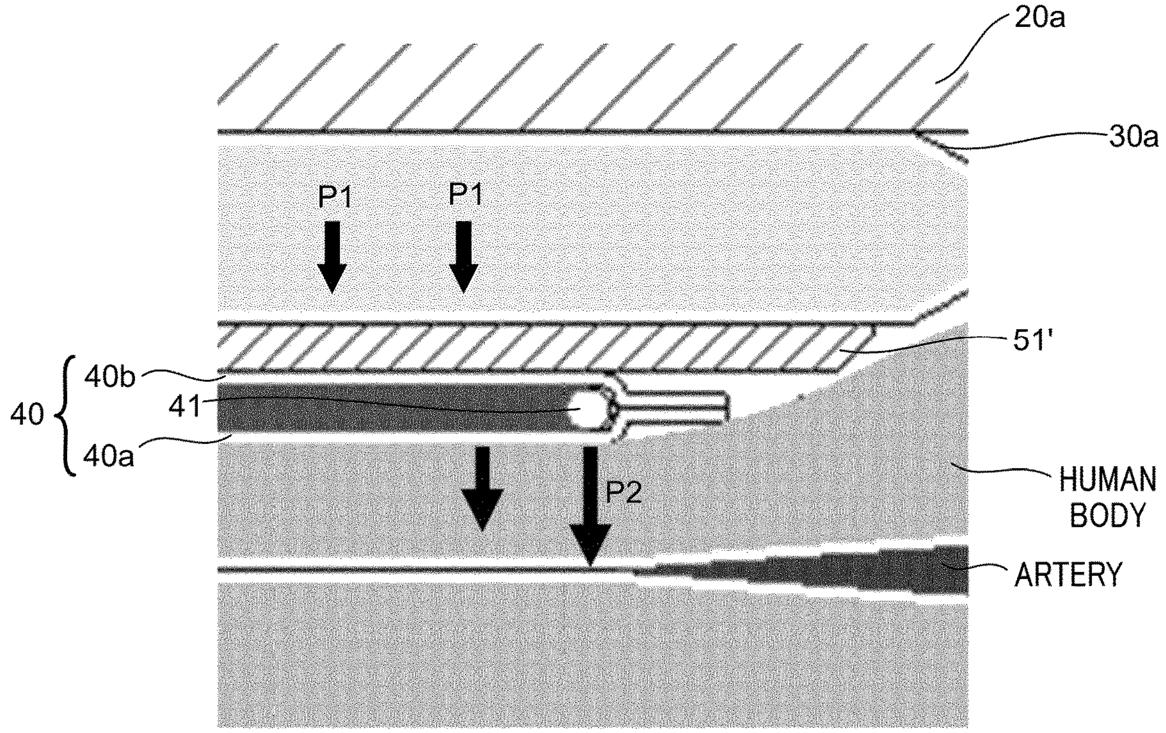
FIG. 14 is an enlarged view of a portion E near the welding pool in FIG. 13, and is a view at the time of blood pressure measurement.

FIG. 13 is a cross-sectional view of a belt, a curler, a pressing cuff, a back plate, and a sensing cuff along a direction in which an artery of a subject extends in a sphygmomanometer 100' of a comparative example. FIG. 14 is an enlarged view of a portion E near the welding pool 41 in FIG. 13, and is a view at the time of blood pressure measurement.

As shown in FIG. 13, in the sphygmomanometer 100' of the comparative example, the width direction dimension W2 of the back plate 51' of the comparative example is set to be longer than the width direction dimension W1 of the sensing cuff 40 in a cross-sectional view along the direction in which the artery extends. Therefore, as shown in FIG. 14, when the pressing force is applied to the sensing cuff 40 as indicated by an arrow P1 by the pressing cuffs 30*a* and 30*b* and the back plate 51' at the time of measurement, the back plate 51' also presses the portion of the hard welding pool 41. As a result, when the sensing cuff 40 is pressed against the human body, a very strong stress is generated as indicated by an arrow P2 near the wall portion of the welding portion where the welding pool 41 at the end portion of the sensing cuff 40 is formed, and a pressure distribution having a large difference between the central portion and the welding portion is generated in the sensing cuff 40, which affects the measurement accuracy. That is, in the comparative example, since the back plate 51' also presses the hard welding pool 41, a strong stress is generated near the welding portion as indicated by an arrow F, and a uniform pressure distribution cannot be obtained as the pressure distribution of the sensing cuff 40. As a result, the air in the sensing cuff 40 cannot sufficiently press the human body even in the central portion of the sensing cuff 40 where the welding pool 41 is not formed, and the pressure pulse wave of the human body becomes small.

(Example 1)

Next, an example in which the pressure distribution in the sensing cuff 40 is measured by the surface pressure sensor using the sphygmomanometer 100 of the present embodiment and the sphygmomanometer 100' of the comparative example will be described. In this example, a surface pressure sensor was installed on the surface of the simulated wrist, the sensing cuff 40 was wound thereon, the sensing cuff 40 was pressed by the back plate 51 (51') and the pressing cuffs 30*a* and 30*b*, and the pressure distribution in the sensing cuff 40 was measured.

In the sphygmomanometer 100' of the comparative example used in the present example, the width direction dimension W0 of the pressing cuff 30*a* shown in FIG. 13 was set as 25 mm, the width direction dimension W2 of the back plate 51' was set as 23 mm, and the width direction dimension W1 of the sensing cuff 40 was set as 15 mm.

In addition, the width direction dimension d of the welding pool 41 (see FIG. 11 for the width direction dimension d of the welding pool 41) in the sphygmomanometer 100' of the comparative example was 0.5 mm, and the first sheet 40*a* and the second sheet 40*b* having a polyurethane (PU) thickness of 0.15 mm were used for the sensing cuff 40. In addition, for the back plate 51', a back plate formed of polypropylene (PP) was used, and the thickness T was set as 0.7 mm.

In the sphygmomanometer 100' of the comparative example as described above, when the pressure distribution in the sensing cuff 40 was measured by the surface pressure sensor, the central portion of the sensing cuff 40 showed a pressure of 100 mmHg in line with the set value. However, the vicinity of the welding portion where the welding pool 41 at the end portion of the sensing cuff 40 was formed showed a very high pressure of around 300 mmHg, and a uniform distribution could not be obtained.

In the sphygmomanometer 100 of the present embodiment used in the present example, the width direction dimension W0 of the pressing cuff 30*a* shown in FIG. 5 was set as 25 mm, the width direction dimension W2 of the back plate 51 was set as 13.5 mm, and the width direction dimension W1 of the sensing cuff 40 was set as 15 mm.

In addition, the width direction dimension d of the welding pool 41 shown in FIG. 11 in the sphygmomanometer 100 of the present embodiment was 0.5 mm, and the first sheet 40*a* and the second sheet 40*b* having a polyurethane (PU) thickness of 0.15 mm were used for the sensing cuff 40. In addition, for the back plate 51, a back plate formed of polypropylene (PP) was used, and the thickness T was set as 0.7 mm. In addition, a C surface of 0.5 mm was formed on an end surface of the back plate 51.

In the sphygmomanometer 100 of the present embodiment as described above, when the pressure distribution in the sensing cuff 40 was measured by the surface pressure sensor, the central portion of the sensing cuff 40 showed a pressure of 100 mmHg in line with the set value. Then, near the welding portion where the welding pool 41 at the end portion of the sensing cuff 40 is formed, although the pressure distribution is slightly high at 120 to 140 mmHg, the pressure distribution is improved as compared with the sphygmomanometer 100' of the comparative example.

(Example 2)

Next, Example 2 will be described in which the pressure pulse wave was measured three times for each of the subject A having a small pressure pulse wave and the subject B having a normal pressure pulse wave using the sphygmomanometer 100 of the present embodiment shown in FIGS. 5, 11, and 12 and the sphygmomanometer 100' of the comparative example shown in FIGS. 13 and 14.

Figure 15:
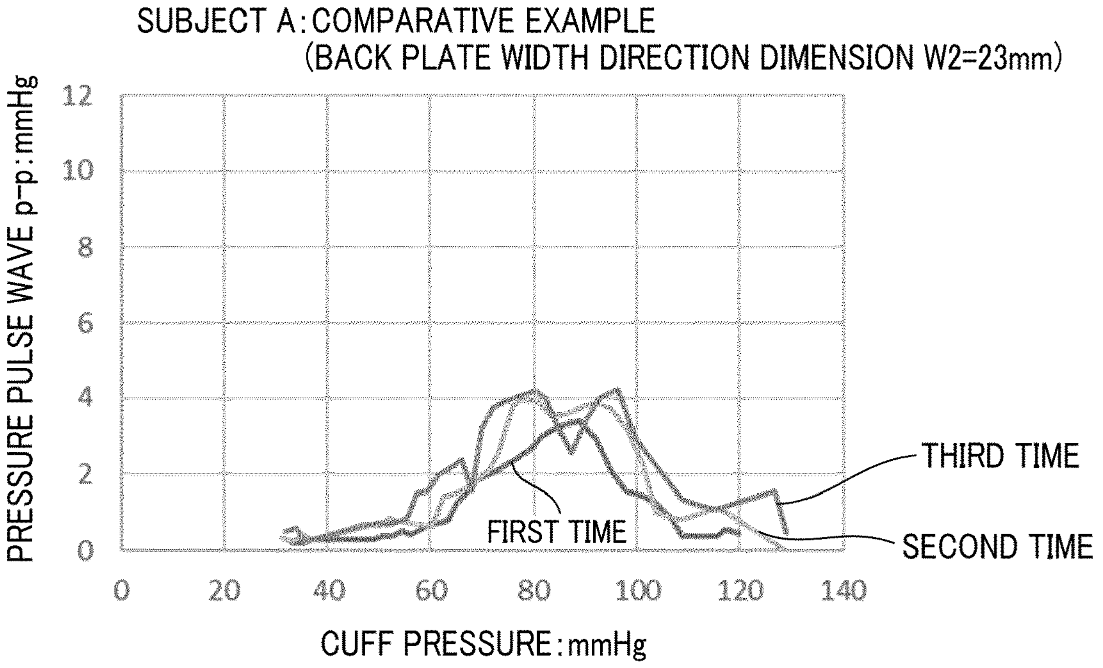
FIG. 15 is a diagram showing a result of measuring the pressure pulse wave three times using the sphygmomanometer of the comparative example for the subject having a small pressure pulse wave.
Figure 16:
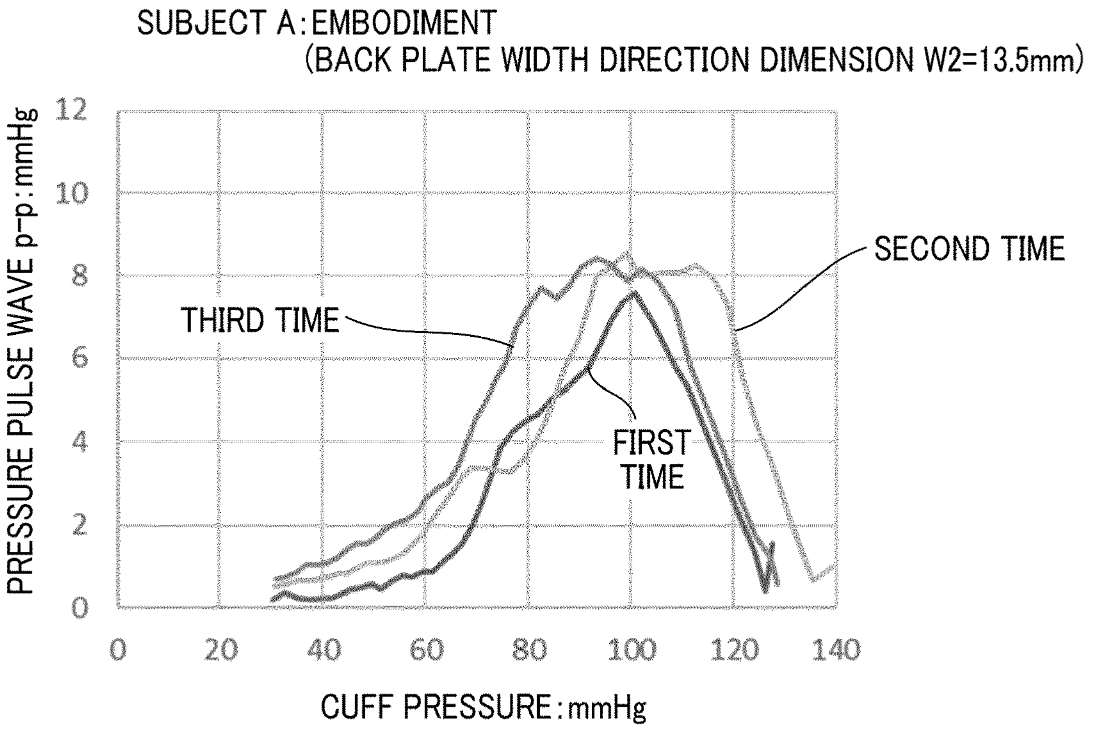
FIG. 16 is a diagram showing a result of measuring the pressure pulse wave three times using the sphygmomanometer of the embodiment for the subject having a small pressure pulse wave.

FIG. 15 is a diagram showing a result of measuring the pressure pulse wave three times using the sphygmomanometer 100' of the comparative example for the subject A having a small pressure pulse wave. FIG. 16 is a diagram showing a result of measuring the pressure pulse wave three times using the sphygmomanometer 100 of the present embodiment for the subject A having a small pressure pulse wave.

As shown in FIG. 15, when the sphygmomanometer 100' of the comparative example is used for the subject A having a small pressure pulse wave, it can be seen that the noise is large and the blood pressure measurement accuracy is lowered. However, when the sphygmomanometer 100 of the present embodiment is used, as shown in FIG. 16, it can be seen that the pressure pulse wave becomes large and the measurement accuracy is improved.

Figure 17:
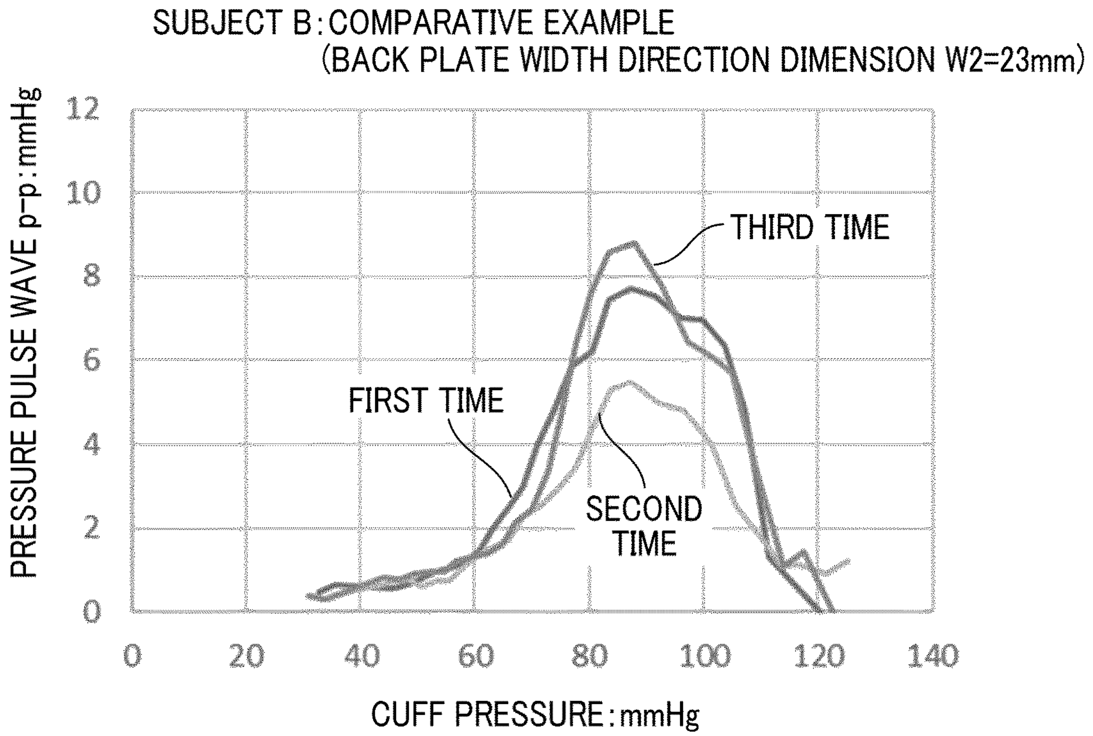
FIG. 17 is a diagram showing a result of measuring the pressure pulse wave three times using the sphygmomanometer of the comparative example for the subject having a normal pressure pulse wave.
Figure 18:
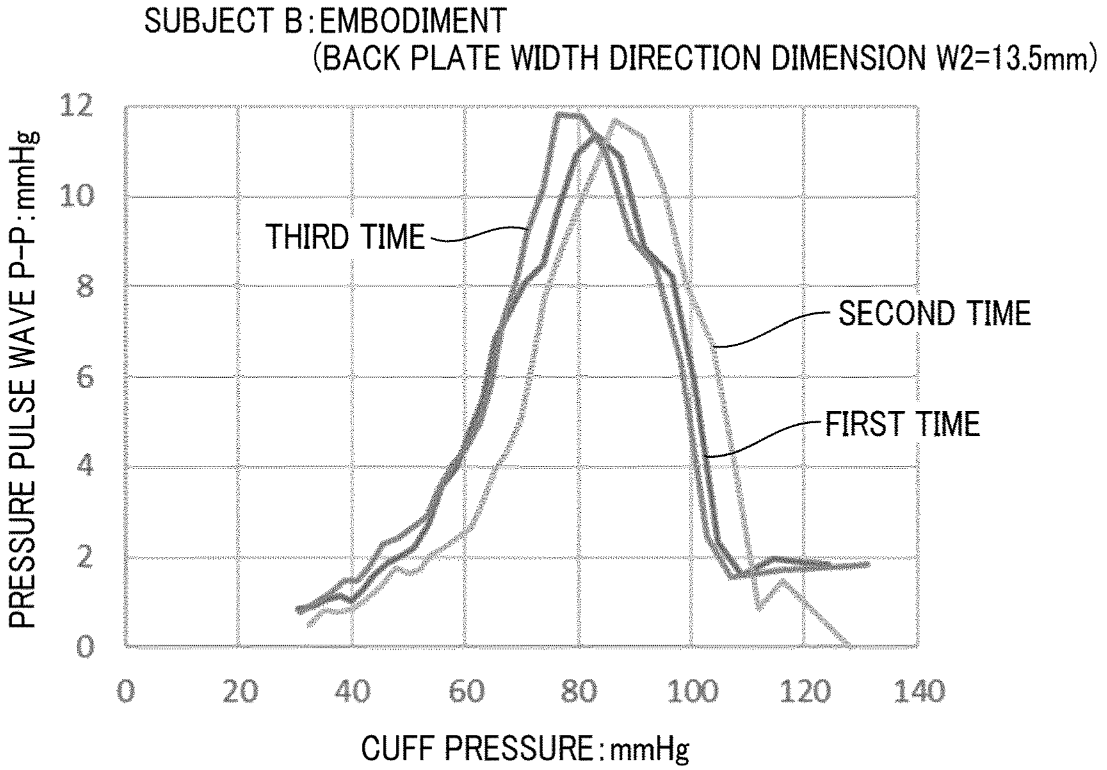
FIG. 18 is a diagram showing a result of measuring the pressure pulse wave three times using the sphygmomanometer of the embodiment for the subject having a normal pressure pulse wave.

FIG. 17 is a diagram showing a result of measuring the pressure pulse wave three times using the sphygmomanometer 100' of the comparative example for the subject B having a normal pressure pulse wave. FIG. 18 is a diagram showing a result of measuring the pressure pulse wave three times using the sphygmomanometer 100 of the present embodiment for the subject B having a normal pressure pulse wave.

As shown in FIG. 17, when the sphygmomanometer 100' of the comparative example is used for the subject B having a normal pressure pulse wave, it can be seen that the pressure pulse wave decreases and the blood pressure measurement accuracy decreases although the noise is not large. However, when the sphygmomanometer 100 of the present embodiment is used, it can be seen that the pressure pulse wave is slightly increased, and the measurement accuracy is improved, as shown in FIG. 18.

(Example 3)

Next, Example 3 in which the human body pressure pulse wave was confirmed by changing the width direction dimension of the back plate 51 in order to confirm the width direction dimension of the optimum back plate 51 in the sphygmomanometer 100 of the present embodiment will be described with reference to FIGS. 19, 20, and 21.

Figure 19:
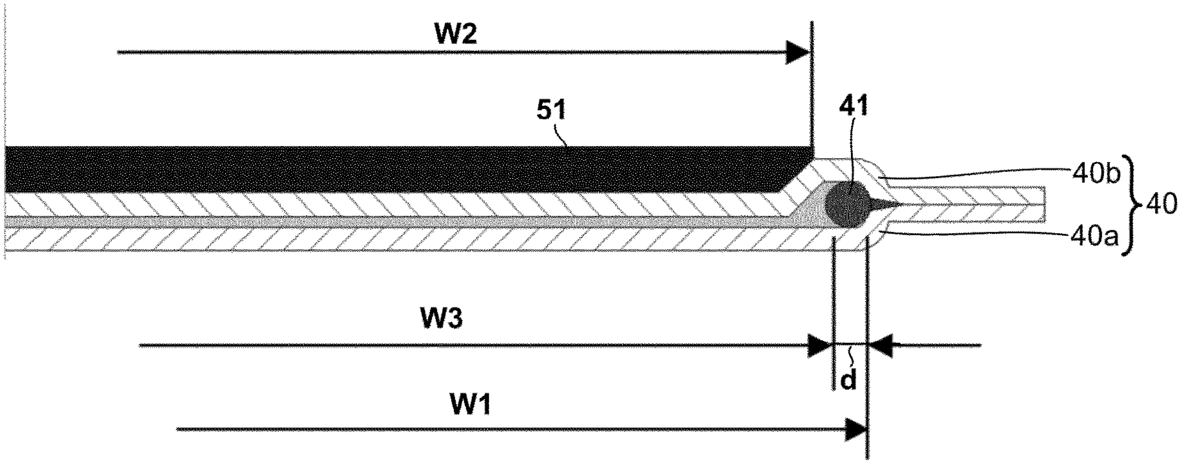
FIG. 19 is a diagram for illustrating a configuration of a sensing cuff and a back plate used in Example 3.
Figure 20:
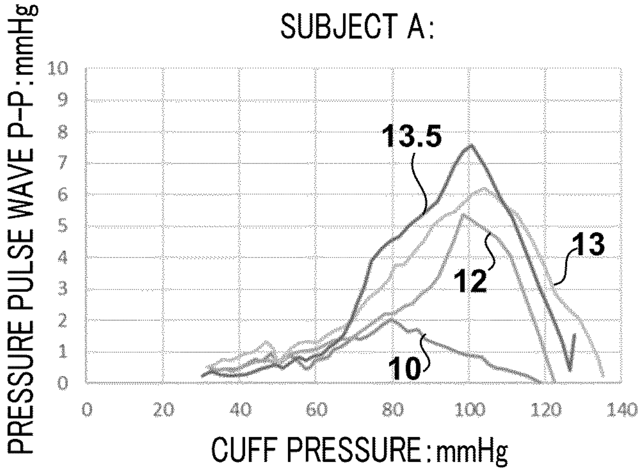
FIG. 20 is a diagram showing measurement results of human body pressure pulse waves for a subject having a small pressure pulse wave in Example 3.
Figure 21:
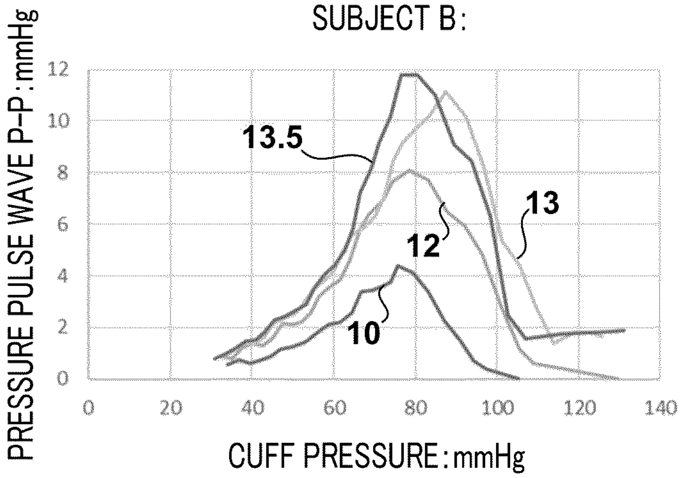
FIG. 21 is a diagram showing measurement results of human body pressure pulse waves for a subject having a normal pressure pulse in Example 3.

FIG. 19 is a diagram for illustrating the configurations of the sensing cuff 40 and the back plate 51 used in the present example, FIG. 20 is a diagram showing the measurement result of the human body pressure pulse wave for the subject A having a small pressure pulse wave, and FIG. 21 is a diagram showing the measurement result of the human body pressure pulse wave for the subject B having a normal pressure pulse.

As shown in FIG. 19, the back plate 51 used in the present example was formed of polypropylene (PP), and four types of 13.5 mm, 13 mm, 12 mm, and 10 mm were used as the width direction dimension W2. The thickness T of the back plate 51 was set as 0.7 mm, and a C surface of 0.5 mm was formed on an end surface of the back plate 51.

In addition, the width direction dimension W1 of the sensing cuff 40 was set as 15 mm, and the effective width direction dimension W3 of the sensing cuff 40 was set as 14 mm. Here, the width direction dimension W1 of the sensing cuff 40 refers to a width direction dimension from one joining end surface, which is an end surface on the internal space side of the sensing cuff 40, to the other joining end surface in a portion where the first sheet 40*a* and the second sheet 40*b* are joined by welding in the cross-sectional view as shown in FIG. 19. In addition, the effective width direction dimension W3 of the sensing cuff 40 refers to a width direction dimension from one end surface protruding toward the internal space of the welding pool 41 to the other end surface.

The width direction dimension d of the welding pool 41 was set as 0.5 mm. For the sensing cuff 40, a first sheet 40*a* and a second sheet 40*b* of polyurethane (PU) having a thickness of 0.15 mm were used.

As shown in FIGS. 20 and 21, in both cases of the subject A and the subject B, it has been found that as the width direction dimension W2 of the back plate 51 is gradually narrowed from 13.5 mm, the pressure pulse wave of the human body also gradually decreases. This is considered to be because as the width direction dimension W2 of the back plate 51 becomes narrower, the air in the sensing cuff 40 escapes laterally and gradually does not effectively press the sensing cuff 40.

Figure 22:
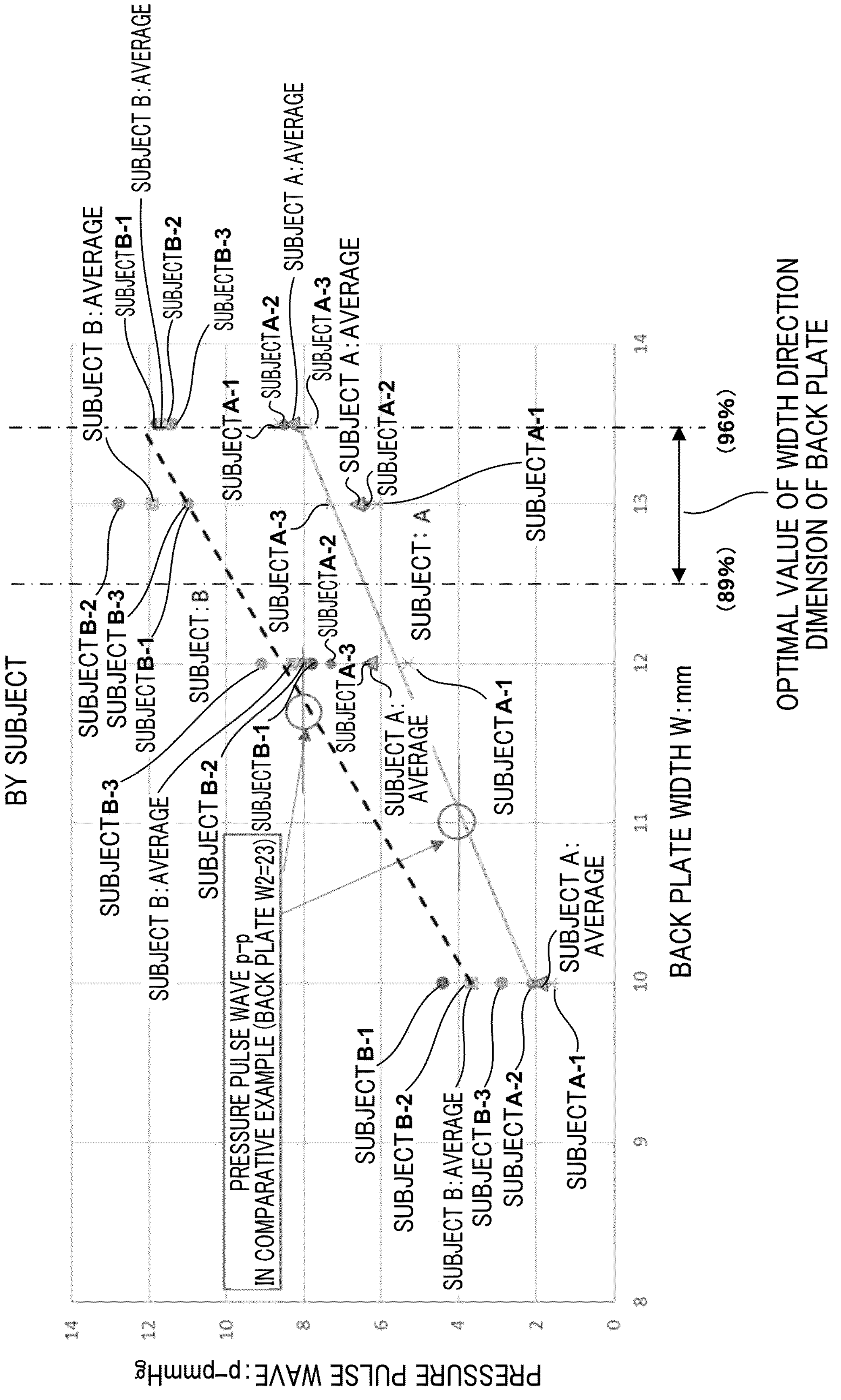
FIG. 22 is a diagram summarizing results obtained by measuring 3 human body pressure pulse waves for each of the subject having a small pressure pulse wave and the subject having a normal pressure pulse while changing the width direction dimension of the back plate and averaging the measured human body pressure pulse waves for each, as described in Example 3.

As described in Example 3, FIG. 22 is a diagram summarizing results obtained by measuring 3 human body pressure pulse waves for each of the subject A having a small pressure pulse wave and the subject B having a normal pressure pulse while changing the width direction dimension W2 of the back plate 51 to 13.5 mm, 13 mm, 12 mm, and 10 mm and averaging the measured human body pressure pulse waves for each.

In FIG. 22, "subject A-1" indicates the first measurement result of the subject A when the width direction dimension W2 of the back plate 51 is set to any one of the above. Hereinafter, similarly, "subject A-2" indicates the second measurement result of the subject A, and "subject A-3" indicates the third measurement result of the subject A. "Subject A: average" indicates an average of three measurement results of the subject A.

Similarly, in FIG. 22, "subject B-1" indicates the first measurement result of the subject B when the width direction dimension W2 of the back plate 51 is set to any one of the above. Hereinafter, similarly, "subject B-2" indicates the second measurement result of the subject B, and "subject B-3" indicates the third measurement result of the subject B. "Subject B: average" indicates an average of three measurement results of the subject B.

As shown in FIG. 22, in the case of the subject A, it can be seen that there is a linear correlation which can be indicated by a solid straight line between the averages of the respective measurement results. In addition, as shown in FIG. 22, also in the case of the subject B, it can be seen that there is a linear correlation which can be indicated by a dotted straight line between the averages of the respective measurement results.

Here, the optimal value of the pressure pulse wave in the subject A in each case was examined, and the optimal width direction dimension W2 of the back plate 51 when such an optimal value of the pressure pulse wave was obtained was obtained from the linear correlation shown in FIG. 22. The width direction dimension W2 of the optimal back plate 51 was 12.5 mm to 13.5 mm. Therefore, it has been found that the following relationship is established between the width direction dimension W2 of the optimal back plate 51 and the effective width direction dimension W3 (14 mm) of the sensing cuff 40.

$$W2 = W3 \times (89 \text{ to } 96\%) \quad \text{(Mathematical 1)}$$

In the cross-sectional view along the direction in which the artery extends, when this relationship is expressed by a relationship between the end surface of the back plate 51 in the width direction of the back plate 51 and the end surface of the welding pool 41, the following is obtained. That is, from the effective width direction dimension W3=14 mm of the sensing cuff 40 and the width direction dimension W2=12.5 mm to 13.5 mm of the optimal back plate 51, it can be seen that a gap of 0.25 mm to 0.75 mm on one side is appropriate for the distance between the end surface of the back plate 51 and the end surface of the welding pool 41. Since the width direction dimension d (see FIG. 12) from the joining end surface of the first sheet 40*a* and the second sheet 40*b* to the end surface of the welding pool 41 formed in the internal space of the sensing cuff 40 is 0.5 mm, the following relationship is established between the width direction dimension d of the welding pool and the distance between the end surface of the back plate 51 and the end surface of the welding pool 41.

$$\text{DISTANCE BETWEEN END SURFACE OF BACK PLATE 51 AND END SURFACE OF WELDING POOL 41} = 0.5\,d \text{ to } 1.5\,d \quad \text{(Mathematical 2)}$$

[Back Plate Thickness and Welding Height]

Figure 23A:
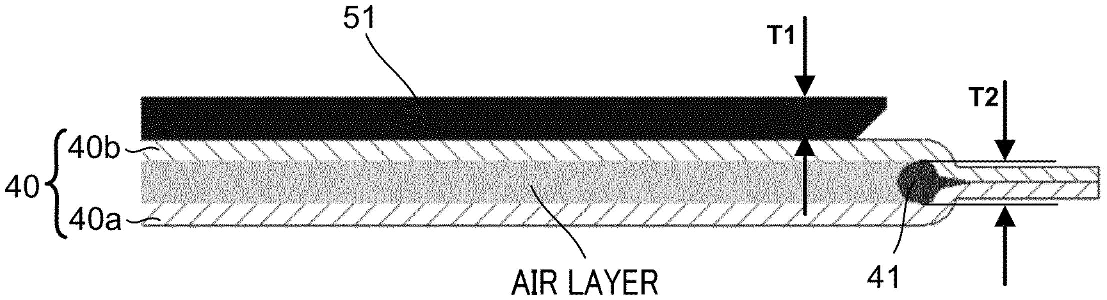
FIG. 23(A) is a view for illustrating the relationship between the thickness of the back plate and the welding height of the welding pool, and is a view before pressing.
Figure 23B:
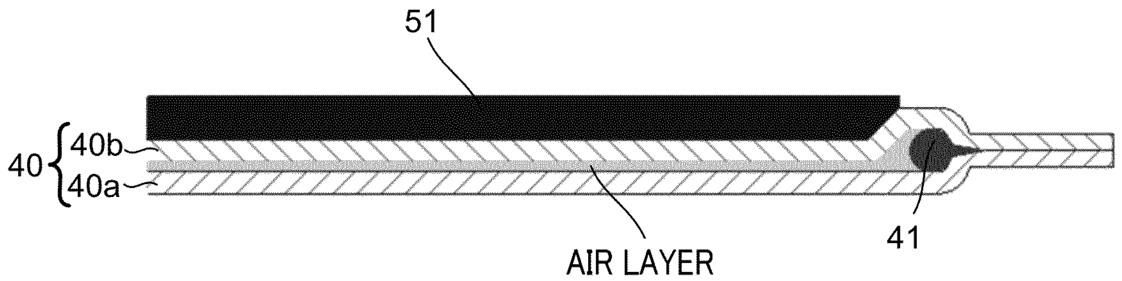
FIG. 23(B) is a view for illustrating the relationship between the thickness of the back plate and the welding height of the welding pool, and is a view at the time of pressing.

Next, the relationship between the thickness of the back plate 51 and the welding height of the welding pool 41 will be described with reference to FIGS. 23(A) and 23(B). FIG. 23(A) is a view for illustrating the relationship between the thickness of the back plate and the welding height of the welding pool, and is a view before pressing. FIG. 23(B) is a view for illustrating the relationship between the thickness of the back plate and the welding height of the welding pool, and is a view at the time of pressing.

In order that the pressing cuffs 30*a* and 30*b* are pressurized, the back plate 51 presses the sensing cuff 40, and the human body is reliably sensed, the thickness T1 of the back plate 51 and the welding height T2 of the welding pool 41 shown in FIG. 23(A) need to have the following relationship.

$$\text{BACK PLATE THICKNESS } T1 \approx \text{WELDING HEIGHT } T2 \quad \text{(Mathematical 3)}$$

When the back plate 51 is too thick, the air layer is likely to be crushed when the sensing cuff 40 is pressed by the back plate 51. In addition, when the back plate 51 is too thin, even when the sensing cuff 40 is pressed by the back plate 51, the sensing cuff 40 cannot be sufficiently pressed by the back plate 51. Therefore, by setting the thickness T1 of the back plate 51 and the welding height T2 of the welding pool 41 to about T1=T2, as shown in FIG. 23(B), the back plate 51 appropriately presses the sensing cuff 40, and the human body can be reliably sensed.

In addition, the welding height T2 of the welding pool 41 varies depending on the welding method, and the material and thickness of the first sheet 40*a* and the second sheet 40*b* of the sensing cuff 40. For example, when the welding height T2 is set to about 0.2 mm which is very low, the thickness T1 of the back plate 51 only needs to be set to 0.2 mm.

As described above, the thickness T1, which is the dimensional width in the direction perpendicular to the width direction of the back plate 51, and the welding height T2, which is the dimensional width of the welding pool 41 in the perpendicular direction thereof, are preferably the same. It should be noted that here, "the same" includes a difference between the thickness T1 of the back plate 51 and the welding height T2 of the welding pool 41 of up to about +20% in consideration of dimensional tolerance.

Next, the relationship between the welding height T2 of the welding pool 41 and the thicknesses of the first sheet 40*a* and the second sheet 40*b* of the sensing cuff 40 is considered as follows. When the first sheet 40*a* and the second sheet 40*b* are too thick, the sensing cuff 40 cannot be sufficiently pressed by the back plate 51. In addition, when the first sheet 40*a* and the second sheet 40*b* are too thin, the air layer is likely to be crushed when the sensing cuff 40 is pressed by the back plate 51. Therefore, as a result of examining the thicknesses of the first sheet 40*a* and the second sheet 40*b* which are not too thick and can measure accurate human body pressure pulse waves by the sensing cuff, it has been found that the thickness of each of the first sheet 40*a* and the second sheet 40*b* only needs not to exceed the welding height T2 of the welding pool 41. For example, when the welding height T2 is set to about 0.2 mm which is very low, each of the first sheet 40*a* and the second sheet 40*b* only needs to be set to 0.15 mm.

As described above, in the present embodiment, since the thickness T1 of the back plate 51 with respect to the welding height T2 of the welding pool 41 and the thicknesses of the first sheet 40*a* and the second sheet 40*b* are appropriately set, it is possible to measure an accurate human body pressure pulse wave by the sensing cuff 40.

It should be noted that in the embodiment described above, what is called a double pressing cuff including the pressing cuff 30*a* and the pressing cuff 30*b* is used as the pressing cuff. However, the present invention is not limited to such an aspect, and the pressing cuff 30*a* may be disposed only on the side facing the artery.

In addition, in the above embodiment, the control unit 63 includes the sub CPU 64 and the main CPU 65, but the control unit 63 may include only the main CPU 65. In addition, although the control unit 63 includes a CPU, the present invention is not limited thereto. The control unit 63 may include a logic circuit (integrated circuit) such as a programmable logic device (PLD) or a field programmable gate array (FPGA).

The above embodiments are exemplary, and various modifications can be made without departing from the scope of the present invention. Each of the plurality of embodiments described above can be established independently, but a combination of the embodiments is also possible. In addition, various characteristics in different embodiments can be independently established, but a combination of characteristics in different embodiments is also possible.

As explained above, according to the sphygmomanometer of one embodiment, when a cross-sectional view is taken in a direction parallel to a direction in which the artery extends, and when a length d is defined at an inside space of the sensing cuff from a welding joint edge between the first sheet and the second sheet to an end surface of the welding pool formed at a time of the welding in the inside space, a distance between an end surface of the back plate at a width direction end of the back plate and the end surface of the welding pool is set to be from 0.5d to 1.5d.

With respect to the sphygmomanometer of this one embodiment, when the width direction dimension of a welding pool formed in the inside space at a time of the welding is set as d, a distance between an end surface of the back plate at a width direction end of the back plate and the end surface of the welding pool is set to be from 0.5d to 1.5d. Therefore, when the sensing cuff is pressed by the back plate, a hard portion where the welding pool is present is not pressed by the back plate, and a strong stress is hardly generated. As a result, a high pressure distribution is not generated in a portion different from a portion where blood pressure information is measured at the site to be measured, and it is possible to measure an accurate human body pressure pulse wave by a sensing cuff.

As explained above, according to the sphygmomanometer of one embodiment, in the cross-sectional view, a dimension in a direction perpendicular to the width direction of the back plate is the same as a dimension of the welding pool in the perpendicular direction.

Here, "the same" includes a difference in the dimensional width of up to about ±20% in consideration of dimensional tolerance.

In the sphygmomanometer according to this one embodiment, in the cross-sectional view, since a dimension in a direction perpendicular to the width direction of the back plate is the same as a dimension of the welding pool in the perpendicular direction, there is no possibility that the air layer of the sensing cuff is likely to be crushed during wearing because the back plate is too thick, or the sensing cuff cannot be sufficiently pushed in during wearing because the back plate is too thin. As a result, it is possible for the back plate to sufficiently push in the sensing cuff, and to reliably measure the human body pressure pulse wave.

In the sphygmomanometer of one embodiment, in the cross-sectional view, a dimension in the perpendicular direction of each of the first sheet and the second sheet is set not to exceed ½ of a dimension of the welding pool in the perpendicular direction.

In the sphygmomanometer according to this one embodiment, in the cross-sectional view, since a dimension in the perpendicular direction of each of the first sheet and the second sheet is set not to exceed ½ of a dimension of the welding pool in the perpendicular direction, the first sheet and the second sheet are not too thick, and it is possible to measure an accurate human body pressure pulse wave by a sensing cuff.

As is clear from the above, in a sphygmomanometer of the present disclosure, since a back plate does not press a portion where a welding pool at an end portion of a sensing cuff is present, it is possible to measure an accurate human body pressure pulse wave by the sensing cuff.

REFERENCE SIGNS LIST

- 10 main body
- 20*a*, 20*b* belt
- 30*a*, 30*b* pressing cuff
- 40 sensing cuff
- 40*a* first sheet
- 40*b* second sheet
- 41 welding pool
- 50 curler
- 51 back plate
- 51*a* end surface of back plate
- 80 lower type welding electrode
- 81 upper type welding electrode
- 82 presser jig
- 100 sphygmomanometer

What is claimed is:

1. A sphygmomanometer comprises:

a sensing cuff including, when being worn on a site to be measured, a first sheet extending in a circumferential direction of the site to be measured to cross an artery passing portion of the site to be measured, and a second sheet facing the first sheet, the sensing cuff having a bag shape formed by welding the first sheet and the second sheet; and a back plate disposed on the second sheet, extending along the circumferential direction of the site to be measured, and conveying a pressing force to the sensing cuff, wherein a width direction dimension of the back plate measured in a width direction perpendicular to the circumferential direction of the site to be measured, is shorter than a width direction dimension of the sensing cuff, and is further shorter than an inner dimension between welding pools formed at end portions of an internal space of the sensing cuff.

2. The sphygmomanometer according to claim 1, wherein when a cross-sectional view is taken in a direction parallel to a direction in which the artery extends, and when a length d is defined at an inside space of the sensing cuff from a welding joint edge between the first sheet and the second sheet to an end surface of the welding pool formed at a time of the welding in the inside space, a distance between an end surface of the back plate at a width direction end of the back plate and the end surface of the welding pool is set to be from 0.5d to 1.5d.

3. The sphygmomanometer according to claim 1, wherein in the cross-sectional view, a dimension in a direction perpendicular to the width direction of the back plate is the same as a dimension of the welding pool in the perpendicular direction.

4. The sphygmomanometer according to claim 3, a dimension in the perpendicular direction of each of the first sheet and the second sheet is set not to exceed ½ of a dimension of the welding pool in the perpendicular direction.

5. The sphygmomanometer according to claim 2, wherein in the cross-sectional view, a dimension in a direction perpendicular to the width direction of the back plate is the same as a dimension of the welding pool in the perpendicular direction.

6. The sphygmomanometer according to claim 5, a dimension in the perpendicular direction of each of the first sheet and the second sheet is set not to exceed ½ of a dimension of the welding pool in the perpendicular direction.

* * * * *